(12) United States Patent
Ketsunee et al.

(10) Patent No.: US 12,083,287 B2
(45) Date of Patent: Sep. 10, 2024

(54) PACKAGING BODY

(71) Applicant: ASAHI INTECC CO., LTD., Seto (JP)

(72) Inventors: Naiyawut Ketsunee, Seto (JP);
Muangmoon Wutthipong, Seto (JP);
Yoshiro Moriguchi, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 466 days.

(21) Appl. No.: 17/387,760

(22) Filed: Jul. 28, 2021

(65) Prior Publication Data

US 2021/0353905 A1 Nov. 18, 2021

Related U.S. Application Data (63) Continuation of application No. PCT/JP2019/045547, filed on Nov. 21, 2019.

(30) Foreign Application Priority Data

Feb. 6, 2019 (JP) .................................. 2019-019652

(51) Int. Cl.
| | | |
|---|---|---|
| B65D 75/30 | (2006.01) | |
| A61M 25/00 | (2006.01) | |
| A61M 25/09 | (2006.01) | |
| B65D 75/58 | (2006.01) | |
| B65D 85/671 | (2006.01) | |

(52) U.S. Cl.
CPC .......... *A61M 25/002* (2013.01); *A61M 25/09* (2013.01); *B65D 75/30* (2013.01); *B65D 75/5855* (2013.01); *B65D 85/671* (2013.01)

(58) Field of Classification Search
CPC ........................... B65D 75/5855; B65D 75/30
See application file for complete search history.

(56) References Cited

U.S. PATENT DOCUMENTS

| | | | | |
|---|---|---|---|---|
| 3,578,239 A | * | 5/1971 | Perlman ................. | B65D 81/34 206/521 |
| 4,176,746 A | * | 12/1979 | Kooi .................. | B65D 75/5855 283/903 |
| 4,318,506 A | * | 3/1982 | Hirsch ................... | B65D 75/30 383/89 |

(Continued)

FOREIGN PATENT DOCUMENTS

| | | |
|---|---|---|
| GB | 2286575 A | 8/1995 |
| JP | 3008738 U | 3/1995 |

(Continued)

OTHER PUBLICATIONS

May 18, 2022 Office Action issued in Chinese Patent Application No. 201980087707.1.

(Continued)

*Primary Examiner* — Mollie Impink (57) ABSTRACT

A packaging body includes first and second sheet members superimposed on each other, and a sticking region formed on an outer periphery of the first and second sheet members. The sticking region has an opening portion in at least one part of the sticking region. The opening portion has an angled, convex shape and includes (i) a non-sticking portion in which the first and second sheet members are not stuck together and (ii) a plurality of first sticking portions that sandwich the non-sticking portion and in which the first and second sheet members are stuck together.

12 Claims, 7 Drawing Sheets

(56) References Cited

U.S. PATENT DOCUMENTS

| | | | | |
|---|---|---|---|---|
| 5,947,288 | A * | 9/1999 | Dykstra | A61B 50/30 206/439 |
| 10,815,042 | B2 * | 10/2020 | Cardin | B65B 61/007 |
| 2006/0200098 | A1 * | 9/2006 | von Falkenhausen | B65D 75/5855 604/289 |
| 2009/0161995 | A1 * | 6/2009 | Henderson | B65D 75/5833 53/469 |
| 2013/0213967 | A1 * | 8/2013 | Kroeyr | B65D 51/00 220/315 |
| 2017/0253403 | A1 * | 9/2017 | Evans | B65B 51/00 |
| 2020/0354111 | A1 * | 11/2020 | Kalihari | B65D 75/008 |

FOREIGN PATENT DOCUMENTS

| | | |
|---|---|---|
| JP | 2003-205972 A | 7/2003 |
| JP | 2008-514517 A | 5/2008 |
| JP | 2011-194128 A | 10/2011 |
| JP | 2012-012086 A | 1/2012 |
| JP | 2012-176767 A | 9/2012 |
| JP | 2015-217969 A | 12/2015 |
| WO | 2016/163428 A1 | 10/2016 |

OTHER PUBLICATIONS

Sep. 8, 2021 Office Action issued in Japanese Patent Application No. 2019-019652.

* cited by examiner

PACKAGING BODY

The present application is a Bypass Continuation of PCT/JP2019/045547, filed Nov. 21, 2019, which is based upon and claims priority from Japanese Application No. 2019-019652 filed on Feb. 6, 2019, the entirety of the prior applications being hereby incorporated by reference into this application.

FIELD

The present disclosure relates to a packaging body.

BACKGROUND

Conventionally, a storage item, in which a long medical member such as a guide wire is stored, is generally sterilized and stored in a packaging body.

For example, Patent Literature 1 describes a packaging body, in which a guide wire storage item is stored (see FIG. 1, etc.).

Patent Literature 1 describes the packaging body wherein two sheet materials are superimposed on each other and the peripheral edges of the sheet materials are sealed to form a storage space for a guide wire storage item.

CITATION LIST

Patent Literature

[Patent Literature 1] Japanese Unexamined Patent Publication No. 2011-194128

SUMMARY

Technical Problem

However, the packaging body described in Patent Literature 1 is problematic in that, since the entire peripheral edges of the sheet materials are sealed with substantially the same width, the sealing strength of the packaging body is sufficiently ensured, but the packaging body cannot be easily opened when the guide wire storage item is taken out from the packaging body.

On the other hand, in consideration of transportation of a packaging body, it is necessary to sufficiently ensure the sealing strength of the packaging body for storing a guide wire storage item.

The disclosed embodiments have been made in response to the above-mentioned problems of the prior art, and an object thereof is to provide a packaging body having sealing strength that can be sufficiently ensured and an opening that can be easily opened.

Solution to Problem

In order to achieve the above object, a first aspect of the disclosed embodiments is characterized in that a packaging body, in which a sticking region with sheet members stuck thereto is formed on an outer periphery thereof, has an opening in at least one part of the sticking region, wherein the opening is formed of: a non-sticking portion having a mountain-like angular shape and having no sheet member stuck thereto; and a plurality of sticking portions formed to sandwich the non-sticking portion and having the sheet members stuck thereto.

A second aspect of the disclosed embodiments is characterized in that in the packaging body of the first aspect, a width of the opening is the same as a width of an area other than the opening in the above sticking region.

Further, a third aspect of the disclosed embodiments is characterized in that in the packaging body of the first aspect or the second aspect, a width in a vicinity of an apex of the angular shape of the sticking portion is smaller than a width in an area(s) other than that in the vicinity of the apex of the angular shape.

Further, a fourth aspect of the disclosed embodiments is characterized in that: in the packaging body of the first aspect or the second aspect, a width of the sticking portion gradually decreases toward an apex of the angular shape of the opening; and a width of the non-sticking portion gradually increases toward the apex of the angular shape of the opening.

Further, a fifth aspect of the disclosed embodiments is characterized in that in any one of the packaging bodies of the first aspect to the fourth aspect, the sticking portion has an angle with respect to a base thereof, which gradually increases toward an apex of the angular shape of the opening.

Advantageous Effects

According to the first aspect of the disclosed embodiments, the packaging body, in which a sticking region with sheet members stuck thereto is formed on an outer periphery thereof, has an opening in at least one part of the sticking region, wherein the opening has a mountain-like angular shape and is formed of a non-sticking portion with no sheet member stuck thereto and a plurality of sticking portions formed to sandwich the non-sticking portion and having the sheet members stuck thereto. Hence, the sealing strength of the packaging body can be sufficiently ensured and the opening of the packaging body can be easily opened.

Further, according to the second aspect of the disclosed embodiments, in the packaging body of the first aspect, a width of the opening is the same as a width in an area other than the opening in the sticking region. Hence, in addition to the effect of the packaging body of the first aspect, the sealing strength of the packaging body can be sufficiently ensured, and the opening of the packaging body can be more easily opened.

Moreover, according to the third aspect of the disclosed embodiments, in the packaging body of the first aspect or the second aspect, a width in a vicinity of an apex of the angular shape of the sticking portion is smaller than a width in an area other than that in the vicinity of the apex of the angular shape. Hence, in addition to the effect of the packaging body of the first aspect or the second aspect, the opening of the packaging body can be more easily opened.

Moreover, according to the fourth aspect of the disclosed embodiments, in the packaging body of the first aspect or the second aspect, a width of the sticking portion gradually decreases toward an apex of the angular shape of the opening and a width of the non-sticking portion gradually increases toward the apex of the angular shape of the opening. Hence, in addition to the effect of the packaging body of the first aspect or the second aspect, the opening of the packaging body can be more easily opened.

Moreover, according to the fifth aspect of the disclosed embodiments, in any one of the packaging bodies of the first aspect to the fourth aspect, the sticking portion has an angle with respect to a base thereof, which gradually increases toward an apex of the angular shape of the opening. Hence, in addition to the effect of any one of the packaging bodies of the first aspect to the fourth aspect, the opening of the packaging body can be more easily opened.

DETAILED DESCRIPTION OF EMBODIMENTS

Hereinafter, embodiments of the disclosure will be described with reference to the enclosed drawings.

First Embodiment

First, the first embodiment of the disclosed embodiments will be described.

Figure 1:
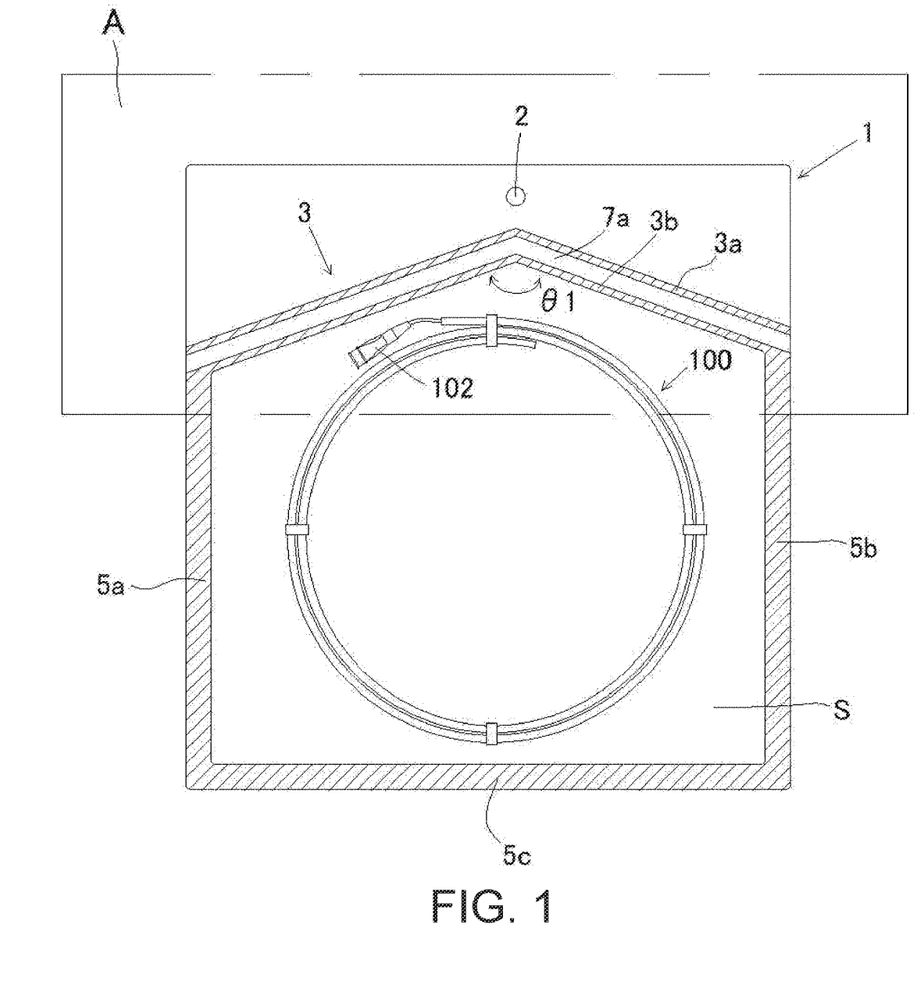
FIG. 1 is an overall plan view of the packaging body of the first embodiment of the disclosed embodiments.
Figure 2:
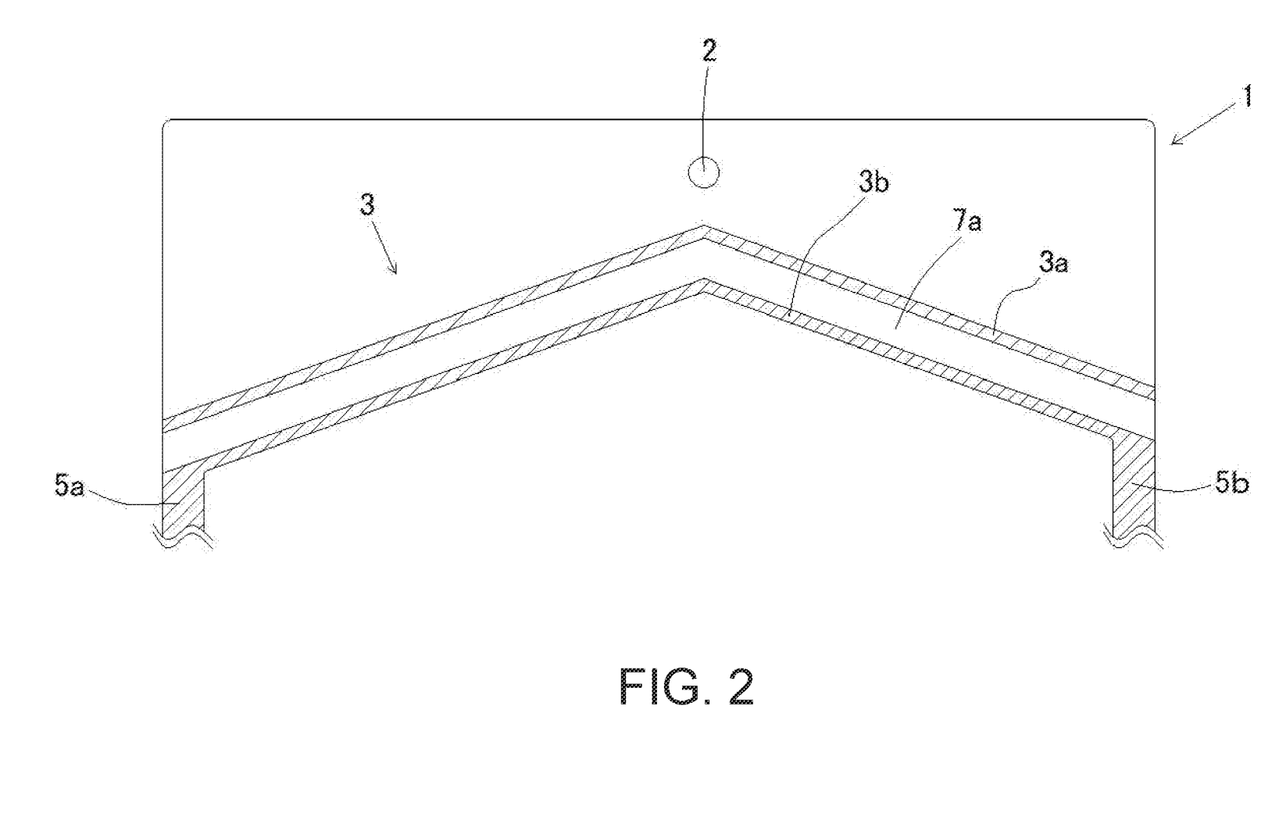
FIG. 2 is an enlarged plan view of section A in FIG. 1.

FIG. 1 is an overall plan view of the packaging body of the first embodiment of the disclosed embodiments. FIG. 2 is an enlarged plan view of section A in FIG. 1.

As shown in FIG. 1 and FIG. 2, a packaging body 1 is a bag for accommodating a medical member storage item 100 in which a long medical member 102 such as a guide wire is stored, and is composed in the form of a bag by superimposing two sheet materials on each other and then bonding their peripheral edges by heat sealing, etc.

Each sheet material is composed of a rectangular soft sheet (flexible sheet) and is formed in the same size.

In the packaging body 1, first, in a state where two sheet materials are superimposed on each other, the left sides, the right sides, and the upper parts of the peripheral edges of the sheet materials are heat-sealed, thereby forming a sealing portion formed of a sticking portion 5a, a sticking portion 5b, and an opening 3.

The seal portion of the opening 3 has a wide-angle, substantially V-shaped angular shape bent so as to be convex toward the upper side of the packaging body 1, and is composed of: a sticking portion 3b connected to the upper ends of the sticking portion 5a and the sticking portion 5b; a non-sticking portion 7a, which is adjacent to the upper side of the sticking portion 3b and to which two sheet materials are not stuck; and a sticking portion 3a adjacent to the upper side of the non-sticking portion 7a.

In addition, the packaging body 1 opens at its base when the medical member storage item 100 is not stored. The base is heat-sealed after storing the medical member storage item 100 in the package body 1, thereby forming a sticking portion 5c.

Storage space S is surrounded by the sticking portion 5a, the sticking portion 5b, the sticking portion 5c, and the sticking portion 3b, so as to have a pentagonal shape in a plan view. The sticking portion 3b has a vertex angle θ1 preferably ranging from 150° to 170°. Further, the sticking portion 3a has a vertex angle also preferably ranging from 150° to 170°.

The two sheet materials composing the packaging body 1 preferably have gas permeability. Specifically, the sheet materials are preferably barrier films that are permeable by sterilizing gases such as ethylene oxide and hydrogen peroxide but impermeable by moisture and bacteria such as bacteria.

Thus, after the medical member storage item 100 is stored in the packaging body 1, the medical member storage item 100 can be sterilized by allowing a sterilizing gas to pass through the storage space S through the sheet materials.

Examples of the constituent materials of such sheet materials, which can be used herein, include polyesters such as polyethylene terephthalate (PET), polyolefins such as polypropylene (PP), polystyrene (PS) and polyethylene (PE), polyvinyl chloride (PVC), polymethyl methacrylate (PMMA), polyether sulfone (PES), polypropylene and ethylene vinyl alcohol (EVOH), polypropylene and polyethylene, and nylon and polypropylene, etc.

Note that, of the sheet materials, a bonding layer may be formed on the sticking portion 3a and the sticking portion 3b of the opening 3. The bonding layer is a layer for heat-sealing the opening 3 in a peelable manner.

The constituent materials of such a bonding layer vary depending on the constituent materials, etc., of the sheet materials. For example, olefin resins such as an ethylene-vinyl acetate resin, an ethylene-acrylic acid resin, an ethylene-vinyl acetate resin, and an ethylene-acrylic acid resin, a vinyl chloride-vinyl acetate copolymer, and a two-component curing type urethane dry laminate adhesive and the like can be used.

Note that a hole 2 for locking the packaging body 1 is formed in the upper part of the packaging body 1.

According to the packaging body 1 of this embodiment, the packaging body, in which a sticking region with sheet members stuck thereto is formed on the outer periphery thereof, has the opening 3 in at least one part of the sticking region, wherein the opening 3 has a mountain-like angular shape and is formed of a non-sticking portion 7a with no sheet member stuck thereto and a plurality of sticking portions 3a and 3b formed to sandwich the non-sticking portion 7a and having the sheet members stuck thereto. Hence, the sealing strength of the packaging body 1 can be sufficiently ensured and the opening 3 of the packaging body 1 can be easily opened.

Second Embodiment

Next, the second embodiment of the disclosed embodiments will be described.

Figure 3:
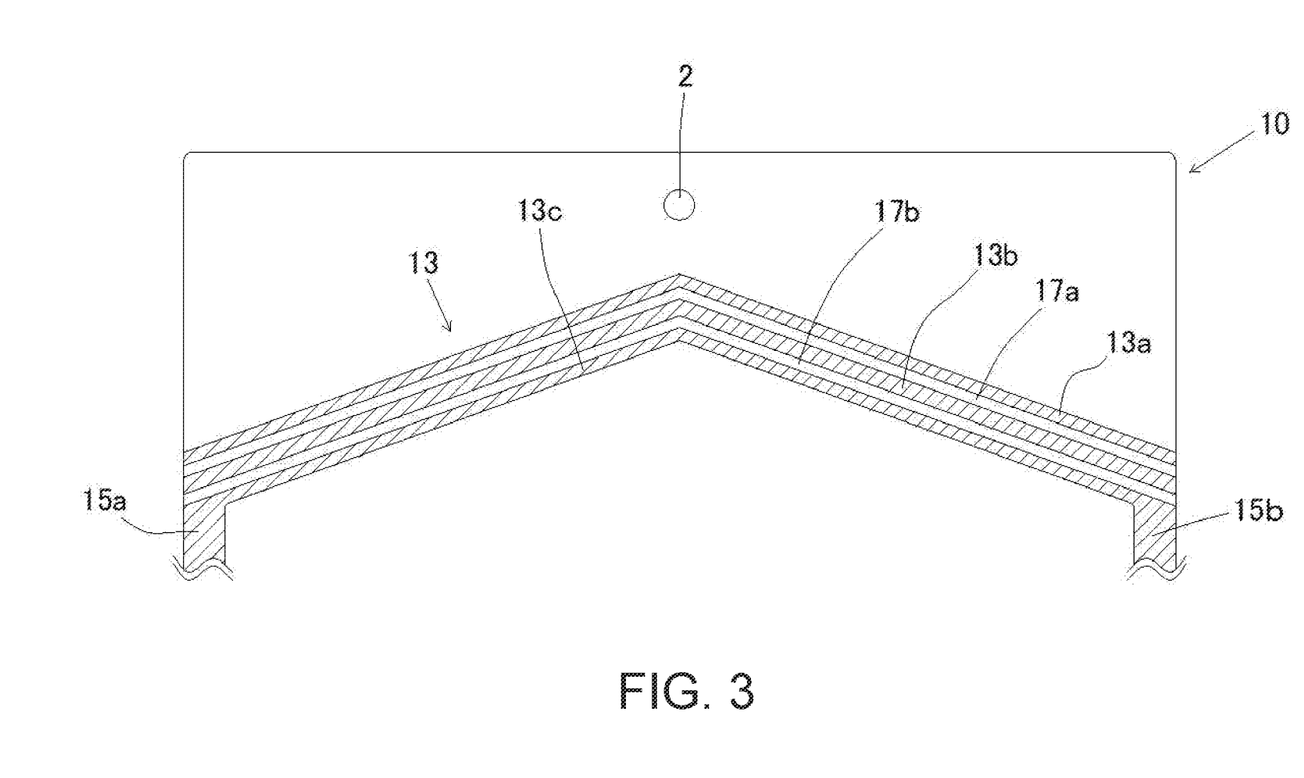
FIG. 3 is a partially enlarged plan view of the packaging body of the second embodiment.

FIG. 3 is a partially enlarged plan view of the packaging body of the second embodiment.

Note that in this embodiment, the same reference numerals are assigned to the same members as those in the first embodiment, and the description thereof will be omitted. The overall plan view of the packaging body of this embodiment is almost the same as that of FIG. 1, and thus will be omitted.

Further, in this embodiment and other embodiments described later, a method(s) for producing a packaging body, the size of sheet materials, the material of the sheet materials, the material of an adhesive when the adhesive is formed on the sheet materials, and the shape of storage space S are the same as those in the first embodiment, and thus descriptions thereof will be omitted in this embodiment and other embodiments described later.

As shown in FIG. 3, a packaging body 10 is a bag for accommodating a medical member storage item 100 and is composed in the form of a bag by superimposing two sheet materials on each other and then bonding the peripheral edges by heat sealing, etc.

The seal portion of an opening 13 has a wide-angle, substantially V-shaped angular shape bent so as to be convex toward the upper side of the packaging body 10, and is composed of: a sticking portion 13c connected to the upper ends of a sticking portion 15a and a sticking portion 15b; a non-sticking portion 17b, which is adjacent to the upper side of the sticking portion 13c and to which two sheet materials are not stuck; a sticking portion 13b adjacent to the upper side of the non-sticking portion 17b; a non-sticking portion 17a, which is adjacent to the upper side of the sticking portion 13b and to which two sheet materials are not stuck; and a sticking portion 13a adjacent to the upper side of the non-sticking portion 17a.

The vertex angle of the sticking portion 3c, the vertex angle of the sticking portion 3b and the vertex angle of the sticking portion 3a preferably range from 150° to 170°.

According to the packaging body 10 of this embodiment, the packaging body, in which a sticking region with sheet members stuck thereto is formed on the outer periphery thereof, has the opening 13 in at least one part of the sticking region, wherein the opening 13 has a mountain-like angular shape and is formed of a non-sticking portion 17a with no sheet member stuck thereto and a plurality of sticking portions 13a and 13b formed to sandwich the non-sticking portion 17a and having the sheet members stuck thereto, a non-sticking portion 17b with no sheet member stuck thereto, and a plurality of sticking portions 13b and 13c formed to sandwich the non-sticking portion 17b and having the sheet members stuck thereto. Hence, the sealing strength of the packaging body 10 can be sufficiently ensured and the opening 13 of the packaging body 1 can be easily opened.

Note that this embodiment describes the number of sticking portions as 3, and the number of non-sticking portions as 2, and the first embodiment describes the number of sticking portions as 2 and the number of non-sticking portions as 1. However, in these embodiments and other embodiments described later, the number of sticking portions may be plural (two or more), and the number of non-sticking portions may be one or more.

Third Embodiment

Next, the third embodiment of the disclosed embodiments will be described.

Figure 4:
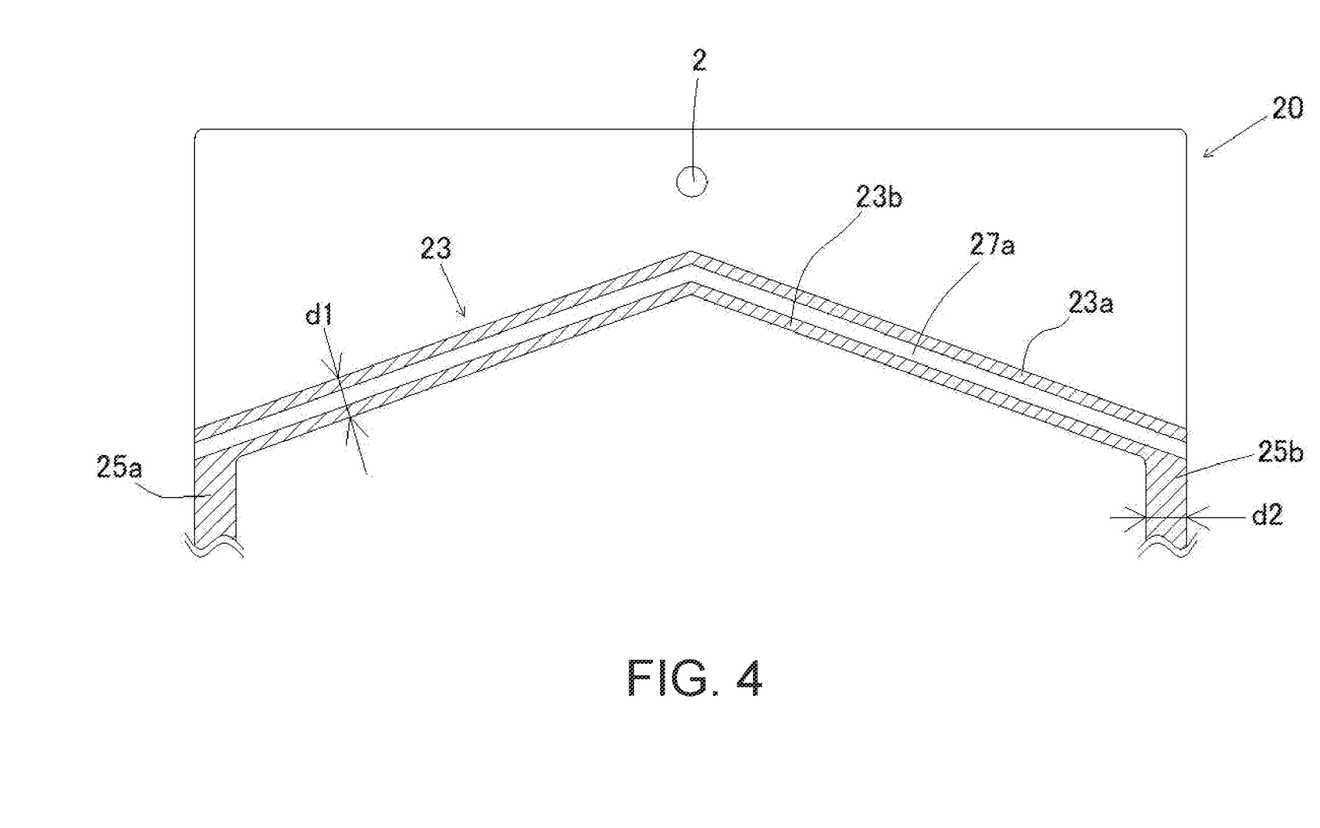
FIG. 4 is a partially enlarged plan view of the packaging body of the third embodiment.

FIG. 4 is a partially enlarged plan view of the packaging body of the third embodiment.

Note that in this embodiment, the same reference numerals are assigned to the same members as those in the first embodiment, and the description thereof will be omitted. The overall plan view of the packaging body of this embodiment is almost the same as that of FIG. 1, and thus will be omitted.

As shown in FIG. 4, a packaging body 20 is a bag for accommodating a medical member storage item 100 and is composed in the form of a bag by superimposing two sheet materials on each other and then bonding the peripheral edges by heat sealing, etc.

A seal portion of an opening 23 has a wide-angle, substantially V-shaped angular shape bent so as to be convex toward the upper side of the packaging body 20, and is composed of: a sticking portion 23b connected to the upper ends of a sticking portion 25a and a sticking portion 25b; a non-sticking portion 27a, which is adjacent to the upper side of the sticking portion 23b and to which two sheet materials are not stuck; and a sticking portion 23a adjacent to the upper side of the non-sticking portion 27a.

Note that the width d1 of the opening 23 of this embodiment is the same as the width d2 of the sticking portion 25a and the sticking portion 25b.

Moreover, the vertex angle of the sticking portion 23b and the vertex angle of the sticking portion 23a preferably range from 150° to 170°.

According to the packaging body 20 of this embodiment, the packaging body, in which a sticking region with sheet members stuck thereto is formed on the outer periphery thereof, has the opening 23 in at least one part of the sticking region, wherein the opening 23 has a mountain-like angular shape, is formed of a non-sticking portion 27a with no sheet member stuck thereto and a plurality of sticking portions 23a and 23b formed to sandwich the non-sticking portion 27a and having the sheet members stuck thereto, and has the width d1 that is the same as the width d2 of the sticking portion 25a and the sticking portion 25b. Hence, the sealing strength of the packaging body 20 can be sufficiently ensured and the opening 23 of the packaging body 20 can be even more easily opened.

Fourth Embodiment

Next, the fourth embodiment of the disclosed embodiments will be described.

Figure 5:
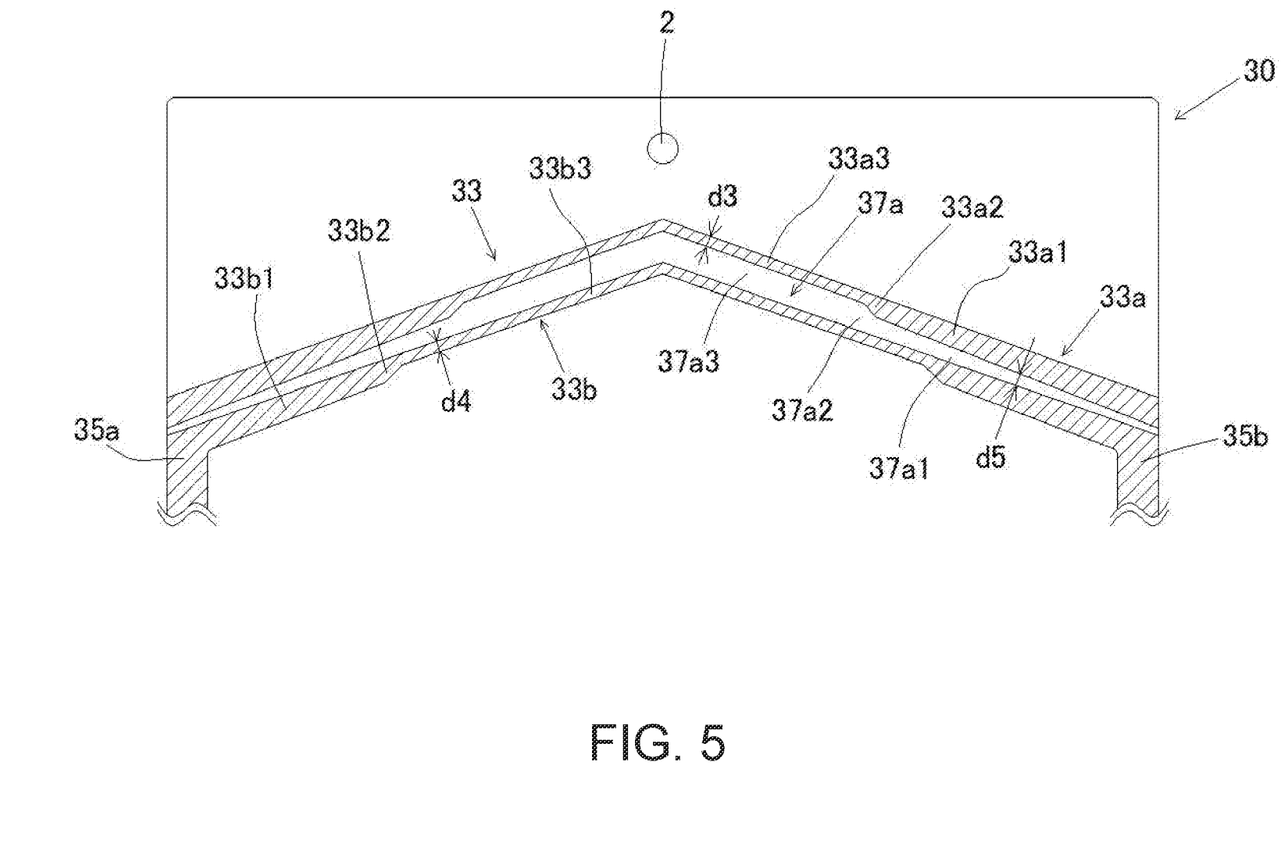
FIG. 5 is a partially enlarged plan view of the packaging body of the fourth embodiment.

FIG. 5 is a partially enlarged plan view of the packaging body of the fourth embodiment.

Note that also in this embodiment, the same reference numerals are assigned to the same members as those in the first embodiment, and the description thereof will be omitted. The overall plan view of the packaging body of this embodiment is almost the same as that of FIG. 1, and thus will be omitted.

As shown in FIG. 5, a packaging body 30 is a bag for accommodating a medical member storage item 100 and is composed in the form of a bag by superimposing two sheet materials on each other and then bonding the peripheral edges by heat sealing, etc.

A seal portion of an opening 33 has a wide-angle, substantially V-shaped angular shape bent so as to be convex toward the upper side of the packaging body 30, and is composed of: a sticking portion 33b connected to the upper ends of a sticking portion 35a and a sticking portion 35b; a non-sticking portion 37a, which is adjacent to the upper side of the sticking portion 33b and to which two sheet materials are not stuck; and a sticking portion 33a adjacent to the upper side of the non-sticking portion 37a.

Note that the width d4 of the sticking portion 33b of this embodiment, specifically, the width d4 in the vicinity of the apex of the angular shape is smaller than that in other areas.

Specifically, the sticking portion 33b is composed of: a sticking portion 33b1 having the width d4 that is the largest at the connection part with the upper end of the sticking portion 35a or the sticking portion 35b and gradually decreases from there to the apex; a sticking portion 33b2 connected to the sticking portion 33b1 and having the width d4 that decreases stepwise; and a sticking portion 33b3 connected to the sticking portion 33b2 and having the width d4 kept at the same width toward the apex.

Further, the width d3 of the sticking portion 33a of this embodiment, specifically, the width d3 in the vicinity of the apex of the angular shape is smaller than that in other areas.

Specifically, the sticking portion 33a is composed of: a sticking portion 33a1 having the width d3 that is the largest at the left end part and the right end part and gradually decreases from there to the apex; a sticking portion 33a2 connected to the sticking portion 33a1 and having the width d3 that decreases stepwise; and a sticking portion 33a3 connected to the sticking portion 33a2 and having the width d3 kept at the same width toward the apex.

Further, the width d5 of the non-sticking portion 37a of this embodiment, specifically, the width d5 in the vicinity of the apex of the angular shape is larger than that in other areas.

Specifically, the non-sticking portion 37a is composed of: a non-sticking portion 37a1 having the width d5 that is the smallest at the left end part and the right end part and gradually increases from there to the apex; a non-sticking portion 37a2 connected to the non-sticking portion 37a1 and having the width d5 that increases stepwise; and a sticking portion 37a3 connected to the non-sticking portion 37a2 and having the width d5 kept at the same width toward the apex.

Note that the vertex angle of the sticking portion 33b and the vertex angle of the sticking portion 33a preferably range from 150° to 170°.

According to the packaging body 30 of this embodiment, the packaging body, in which a sticking region with sheet members stuck thereto is formed on the outer periphery thereof, has an opening 33 in at least one part of the sticking region, wherein the opening 33 has a mountain-like angular shape and is formed of the non-sticking portion 37a with no sheet member stuck thereto and a plurality of sticking portions 33a and 33b formed to sandwich the non-sticking portion 37a and having the sheet members stuck thereto, and the width d4 of the sticking portion 33b and the width d3 of the sticking portion 33a, specifically, the widths in the vicinity of the apex of the angular shape are smaller than those in other areas. Hence, the sealing strength of the packaging body 30 can be sufficiently ensured and the opening 33 of the packaging body 30 can be even more easily opened.

Fifth Embodiment

Next, the fifth embodiment of the disclosed embodiments will be described.

Figure 6:
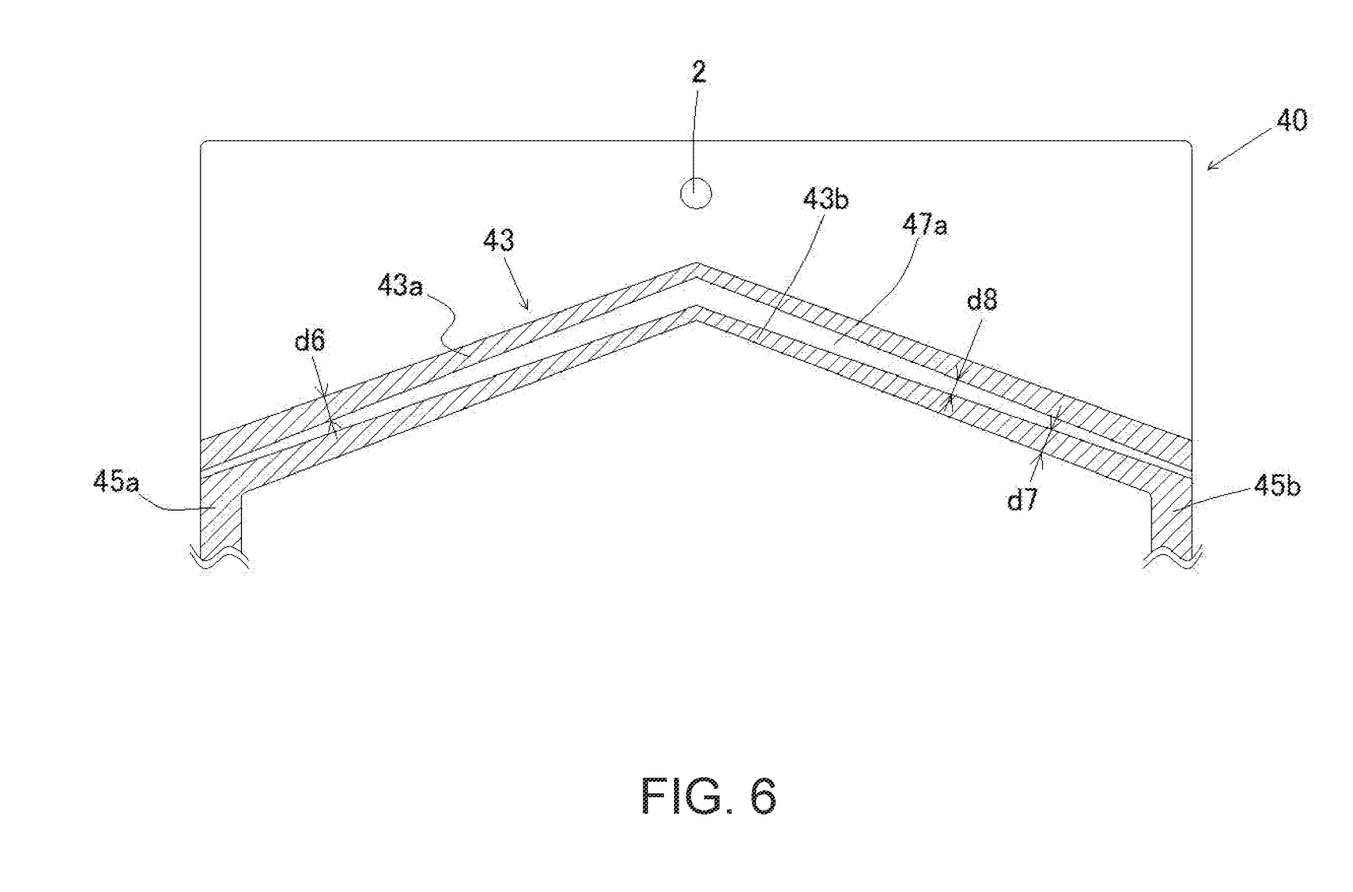
FIG. 6 is a partially enlarged plan view of the packaging body of the fifth embodiment.

FIG. 6 is a partially enlarged plan view of the packaging body of the fifth embodiment.

Note that also in this embodiment, the same reference numerals are assigned to the same members as those in the first embodiment, and the description thereof will be omitted. The overall plan view of the packaging body of this embodiment is almost the same as that of FIG. 1, and thus will be omitted.

As shown in FIG. 6, a packaging body 40 is a bag for accommodating a medical member storage item 100 and is composed in the form of a bag by superimposing two sheet materials on each other and then bonding the peripheral edges by heat sealing, etc.

A seal portion of an opening 43 has a wide-angle, substantially V-shaped angular shape bent so as to be convex toward the upper side of the packaging body 40, and is composed of: a sticking portion 43b connected to the upper ends of a sticking portion 45a and a sticking portion 45b; a non-sticking portion 47a, which is adjacent to the upper side of the sticking portion 43b and to which two sheet materials are not stuck; and a sticking portion 43a adjacent to the upper side of the non-sticking portion 47a.

Note that the width d7 of the sticking portion 43b of this embodiment gradually decreases toward the apex of the angular shape of the opening 43.

The width d6 of the sticking portion 43a of this embodiment also gradually decreases toward the apex of the angular shape of the opening 43.

On the other hand, the width d8 of the non-sticking portion 47a of this embodiment gradually increases toward the apex of the angular shape of the opening 43.

Note that the vertex angle of the sticking portion 43b and the vertex angle of the sticking portion 43a preferably range from 150° to 170°.

According to the packaging body 40 of this embodiment, the packaging body, in which a sticking region with sheet members stuck thereto is formed on the outer periphery thereof, has the opening 43 in at least one part of the sticking region, wherein the opening 43 has a mountain-like angular shape and is formed of the non-sticking portion 47a with no sheet member stuck thereto and a plurality of sticking portions 43a and 43b formed to sandwich the non-sticking portion 47a and having the sheet members stuck thereto, and the width d6 of the sticking portion 43b and the width d7 of the sticking portion 43a gradually decrease toward the apex of the angular shape of the opening 43, and the width 8 of the non-sticking portion 47a gradually increases toward the apex of the angular shape of the opening 43. Hence, the sealing strength of the packaging body 40 can be sufficiently ensured and the opening 43 of the packaging body 40 can be even more easily opened.

Sixth Embodiment

Next, the sixth embodiment of the disclosed embodiments will be described.

Figure 7:
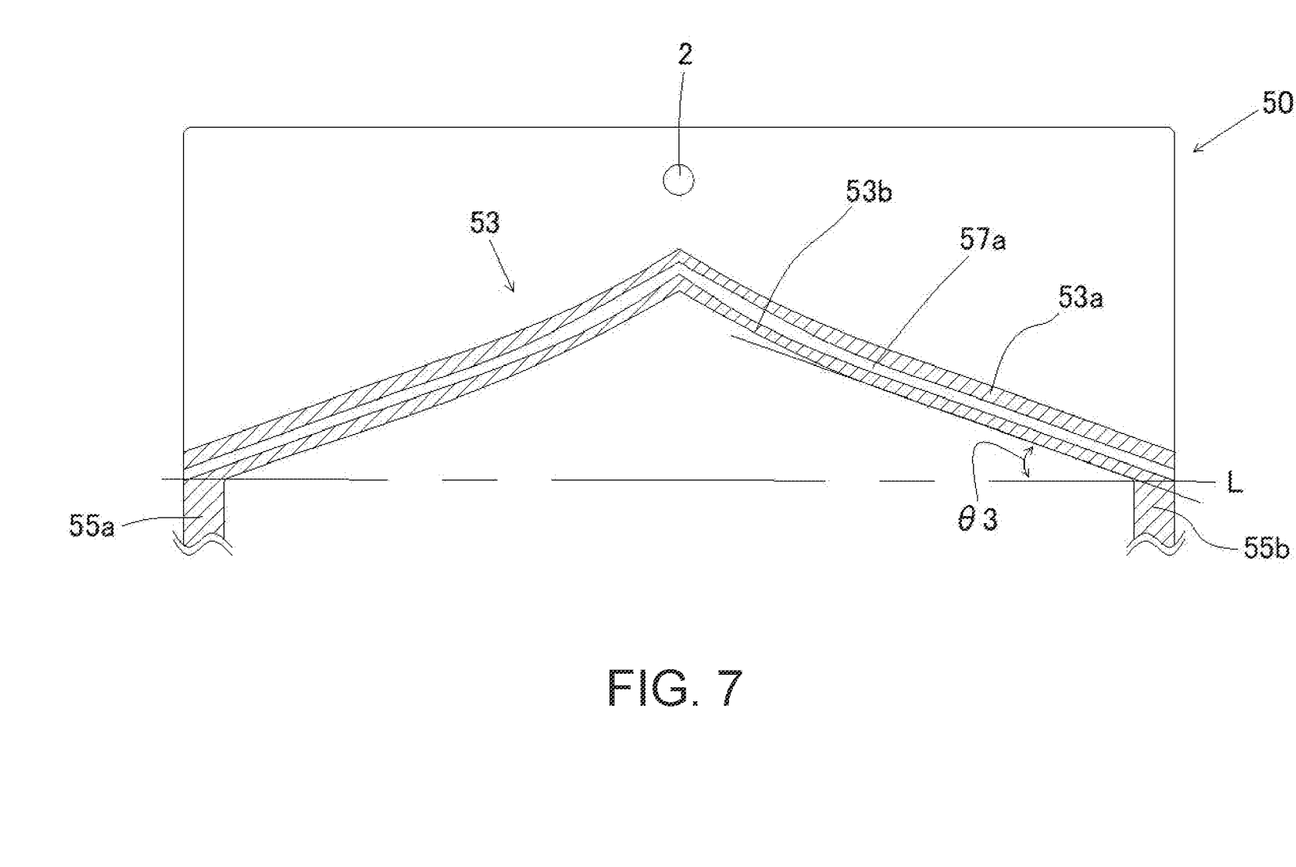
FIG. 7 is a partially enlarged plan view of the packaging body of the sixth embodiment.

FIG. 7 is a partially enlarged plan view of the packaging body of the sixth embodiment.

Note that also in this embodiment, the same reference numerals are assigned to the same members as those in the first embodiment, and the description thereof will be omitted. The overall plan view of the packaging body of this embodiment is almost the same as that of FIG. 1, and thus will be omitted.

As shown in FIG. 7, a packaging body 50 is a bag for accommodating a medical member storage item 100 and is composed in the form of a bag by superimposing two sheet materials on each other and then bonding the peripheral edges by heat sealing, etc.

A seal portion of an opening 53 has a wide-angle, substantially V-shaped angular shape bent so as to be convex toward the upper side of the packaging body 50, and is composed of: a sticking portion 53b connected to the upper ends of a sticking portion 55a and a sticking portion 55b; a non-sticking portion 57a, which is adjacent to the upper side of the sticking portion 53b and to which two sheet materials are not stuck; and a sticking portion 53a adjacent to the upper side of the non-sticking portion 57a.

Note that the sticking portion 53b has a vertex angle θ3 with respect to the base L thereof, which gradually increases toward the apex of the angular shape of the opening 53.

In addition, the sticking portion 53a and the non-sticking portion 57a also have a vertex angle θ3 with respect to the base L thereof, which gradually increases toward the apex of the angular shape of the opening 53.

Note that the vertex angle of the sticking portion 53b and the vertex angle of the sticking portion 53a preferably range from 150° to 170°.

According to the packaging body 50 of this embodiment, the packaging body, in which a sticking region with sheet members stuck thereto is formed on the outer periphery thereof, has the opening 53 in at least one part of the sticking region, wherein the opening 53 has a mountain-like angular shape and is formed of the non-sticking portion 57a with no sheet member stuck thereto and a plurality of sticking portions 53a and 53b formed to sandwich the non-sticking portion 57a and having the sheet members stuck thereto, and the sticking portion 53a and the sticking portion 53b have a vertex angle θ3 with respect to the base L thereof, which gradually increases toward the apex of the angular shape of the opening 53. Hence, the sealing strength of the packaging body 50 can be sufficiently ensured and the opening 53 of the packaging body 50 can be even more easily opened.

In addition, the feature of the packaging body 50 of this embodiment, such that the angle of each sticking portion with respect to the base thereof gradually increases toward the apex of the angular shape of the opening, is also applicable to the packaging body 30 of the fourth embodiment and the packaging body 40 of the fifth embodiment.

REFERENCE SIGN LIST 1, 10, 20, 30, 40, 50 . . . packaging body
3, 13, 23, 33, 43, 53 . . . opening
3a, 3b, 5a, 5b, 5c, 13a, 13b, 13c, 15a, 15b, 23a, 23b, 25a, 25b, 33a, 33b, 35a, 35b, 43a, 43b, 45a, 45b, 53a, 53b, 55a, 55b . . . sticking portion
7a, 17a, 27a, 37a, 47a, 57a . . . non-sticking portion
100 . . . medical member storage item
L . . . base

The invention claimed is:

1. A packaging body comprising:
first and second sheet members superimposed on each other;
a sticking region formed on an outer periphery of the first and second sheet members;
an opening portion extending between first and second ends of the sticking region; and
a seal portion sealing the opening portion, wherein the seal portion includes
  a first sticking portion having a mountain-like angular shape so as to be convex outwardly and connected to the first and second ends of the sticking region,
  a first non-sticking portion formed in a mountain-like angular shape so as to be convex outwardly and adjacent to an outside of the first sticking portion, the first non-sticking portion spaced apart from the first and second ends of the sticking region, and
  a second sticking portion formed in a mountain-like angular shape so as to be convex outwardly and adjacent to an outside of the first non-sticking portion, the second sticking portion spaced apart from the first and second ends of the sticking region and from the first sticking portion, and
both ends of the second sticking portion are spaced apart from the first sticking portion and the first and second ends of the sticking region.

2. The packaging body according to claim 1, wherein
a width in an apex of the angular shape of each of the first sticking portion and the second sticking portion is smaller than a width of the angular shape of each of the first sticking portion and the second sticking portion in an area other than the apex, and
a width in an apex of the angular shape of the first non-sticking portion is larger than a width in an area other than the apex of the angular shape of the first non-sticking portion.

3. The packaging body according to claim 2, wherein the seal portion further includes
  a second non-sticking portion formed in a mountain-like angular shape so as to be convex outwardly and adjacent to an outside of the second sticking portion, the second non-sticking portion spaced apart from the first and second ends of the sticking region and from the first non-sticking portion, and
  a third sticking portion formed in a mountain-like angular shape so as to be convex outwardly and adjacent to an outside of the second non-sticking portion, the third sticking portion spaced apart from the first and second ends of the sticking region, the first sticking portion and the second sticking portion, and
both ends of the third sticking portion are spaced apart from the second sticking portion.

4. The packaging body according to claim 2, wherein
the width of the first sticking portion and the second sticking portion gradually decreases toward the apex of the respective angular shape, and
the width of the first non-sticking portion gradually increases toward the apex of the angular shape of the first non-sticking portion.

5. The packaging body according to claim 4, wherein the seal portion further includes
  a second non-sticking portion formed in a mountain-like angular shape so as to be convex outwardly and adjacent to an outside of the second sticking portion, the second non-sticking portion spaced apart from the first and second ends of the sticking region and from the first non-sticking portion, and
  a third sticking portion formed in a mountain-like angular shape so as to be convex outwardly and adjacent to an outside of the second non-sticking portion, the third sticking portion spaced apart from the first and second ends of the sticking region, the first sticking portion and the second sticking portion, and
both ends of the third sticking portion are spaced apart from the second sticking portion.

6. The packaging body according to claim 2, wherein
the width of the first sticking portion and the second sticking portion decreases stepwise toward the apex of the respective angular shape, and
the width of the first non-sticking portion increases stepwise toward the apex of the angular shape of the first non-sticking portion.

7. The packaging body according to claim 6, wherein the seal portion further includes
  a second non-sticking portion formed in a mountain-like angular shape so as to be convex outwardly and adjacent to an outside of the second sticking portion, the second non-sticking portion spaced apart from the first and second ends of the sticking region and from the first non-sticking portion, and
  a third sticking portion formed in a mountain-like angular shape so as to be convex outwardly and adjacent to an outside of the second non-sticking portion, the third sticking portion spaced apart from the first and second ends of the sticking region, the first sticking portion and the second sticking portion, and
both ends of the third sticking portion are spaced apart from the second sticking portion.

8. The packaging body according to claim 1, wherein
each of the first sticking portion, the second sticking portion and the first non-sticking portion has an angle, with respect to a base thereof, which gradually increases toward an apex of the respective angular shape.

9. The packaging body according to claim 8, wherein the seal portion further includes a second non-sticking portion formed in a mountain-like angular shape so as to be convex outwardly and adjacent to an outside of the second sticking portion, the second non-sticking portion spaced apart from the first and second ends of the sticking region and from the first non-sticking portion, and a third sticking portion formed in a mountain-like angular shape so as to be convex outwardly and adjacent to an outside of the second non-sticking portion, the third sticking portion spaced apart from the first and second ends of the sticking region, the first sticking portion and the second sticking portion, and both ends of the third sticking portion are spaced apart from the second sticking portion.

10. The packaging body according to claim 1, wherein the seal portion further includes a second non-sticking portion formed in a mountain-like angular shape so as to be convex outwardly and adjacent to an outside of the second sticking portion, the second non-sticking portion spaced apart from the first and second ends of the sticking region and from the first non-sticking portion, and a third sticking portion formed in a mountain-like angular shape so as to be convex outwardly and adjacent to an outside of the second non-sticking portion, the third sticking region spaced apart from the first and second ends of the sticking region, the first sticking portion and the second sticking portion, and both ends of the third sticking portion are spaced apart from the second sticking portion.

11. The packaging body according to claim 1, wherein a width of the first non-sticking portion is larger than a width of the first sticking portion.

12. The packaging body according to claim 1, wherein a width of the sticking region is larger than a width of the first sticking portion.

\* \* \* \* \*